United States Patent
Palasis

(10) Patent No.: US 7,060,051 B2
(45) Date of Patent: Jun. 13, 2006

(54) MULTI-BALLOON CATHETER WITH HYDROGEL COATING

(75) Inventor: Maria Palasis, Wellesley, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/253,597

(22) Filed: Sep. 24, 2002

(65) Prior Publication Data

US 2004/0059290 A1    Mar. 25, 2004

(51) Int. Cl.
*A61M 29/00* (2006.01)
(52) U.S. Cl. .............................. 604/101.01
(58) Field of Classification Search ............. 604/96.01, 604/49.01, 101.01, 101.13, 109.05, 103.06, 604/509, 101.02, 101.03, 101.04, 101.05
See application file for complete search history.

(56) References Cited

U.S. PATENT DOCUMENTS

| | | | | |
|---|---|---|---|---|
| 4,705,502 A | * | 11/1987 | Patel | 604/544 |
| 4,976,692 A | * | 12/1990 | Atad | 604/101.03 |
| 5,304,121 A | * | 4/1994 | Sahatjian | 604/509 |
| 5,397,307 A | * | 3/1995 | Goodin | 604/103.07 |
| 5,674,192 A | | 10/1997 | Sahatjian et al. | |
| 5,817,046 A | * | 10/1998 | Glickman | 604/5.04 |
| 5,843,089 A | | 12/1998 | Sahatjian et al. | |
| 5,954,706 A | | 9/1999 | Sahatjian | |

OTHER PUBLICATIONS

Palasis et al., 1997, "Site-Specific Drug Delivery from Hydrogel Coated Angioplasty Catheters," *Proceed. Int'l Symp. Control. Rel. Bioact. Mater.*, 24:825-826.
Palasis et al., 2002, "Analysis of Adenoviral Transport Mechanisms in the Vessel Wall and Optimization of Gene Transfer Using Local Delivery Catheters," *Human Gene Therapy* 11:237-246.
Perlman et al., 1997, "Evidence for rapid onset of apoptosis in medial smooth muscle cells after balloon injury," *Circulation* 95:981-987.

* cited by examiner

*Primary Examiner*—Sharon Kennedy
(74) *Attorney, Agent, or Firm*—Jones Day

(57) ABSTRACT

In one aspect of the invention a multi-balloon catheter, such as a double-balloon catheter, with coating comprising a hydrogel polymer on the exterior surface of the occlusion balloons is provided. The balloons may be inflated inside the lumen to occlude a plaque-affected segment of the lumen thereby forming a lumen space between the balloons, wherein this plaque-affected lumen segment may be treated with a biologically active agent. The presence of the coating can reduce de-nuding of healthy endothelial lumen tissue after contact with the inflated balloons during the occlusion. In another aspect of the invention, a method is provided for using a multi-balloon catheter having a coating comprising a hydrogel polymer for treating a plaque-affected lumen segment, the method reducing the subsequent de-nuding or injury to healthy endothelial tissue that is contacted by the balloon during occlusion.

34 Claims, 3 Drawing Sheets

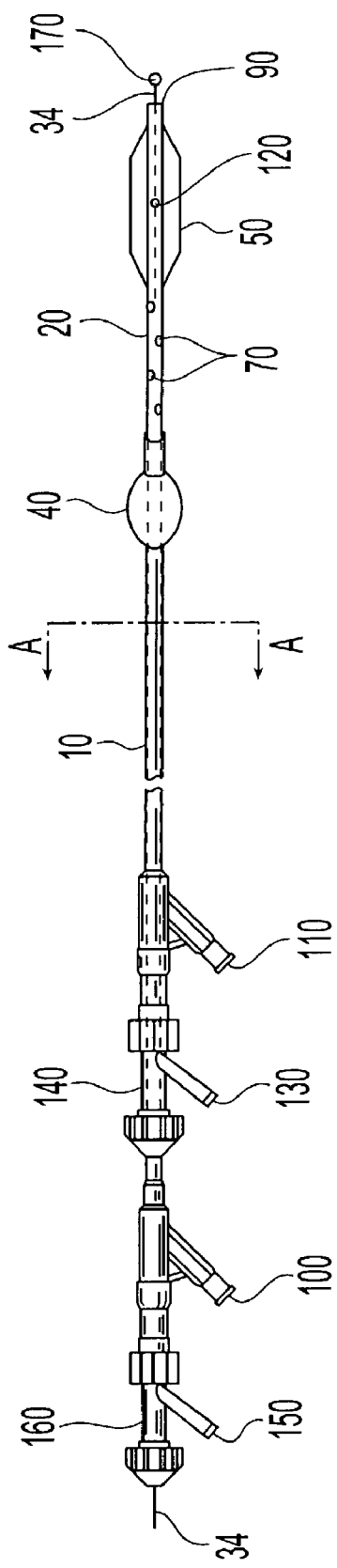
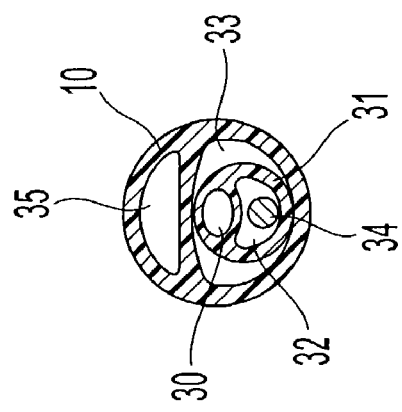
Fig. 1
Fig. 2

MULTI-BALLOON CATHETER WITH HYDROGEL COATING

FIELD OF THE INVENTION

The present invention relates to catheters which may be inserted into body lumens for delivery of biologically active agents. More particularly, the invention relates to catheters having inflatable balloons for occluding body lumens and delivering therapeutic, biologically active agents to a portion of the occluded body lumen.

BACKGROUND OF THE INVENTION

Atherosclerotic disease can cause the build-up of plaque deposits in a localized portion of an arterial vessel. As the deposition increases, the inner diameter of the vessel becomes smaller (stenosis occurs) and impedes blood flow through the vessel. This reduction in blood throughput is harmful to the body and must be corrected. One method of correcting this arterial stenosis is to perform angioplasty using a balloon catheter, which involves inserting a catheter having at least a dilatation balloon into the stenotic area of the artery, inflating this balloon and expanding the inner diameter of the plaque-ridden segment of the artery.

An alternative variation of the above angioplasty method employs a catheter having two spaced-apart occlusion balloons whereby one of the balloons is a dilatation balloon used to expand the plaque-affected segment of the artery. Catheters having double occlusion balloons are disclosed, for example, in U.S. Pat. Nos. 5,836,967 and 5,279,546. After an initial expansion of the stenotic segment of the artery, the dilatation balloon is deflated and the catheter is manipulated and positioned such that the affected segment of the artery is between the two balloons. The two balloons are simultaneously pressurized and inflated, forming an enclosed, sealed space wherein the affected portion of the artery is contained within this space. In other words an occluded portion in the artery or lumen is formed. The catheter portion between the two balloons has a hole or plurality of holes for delivery of biologically active agents therethrough to variously treat the affected arterial segment. Thus, unlike a catheter having only a single balloon, the double-balloon catheter advantageously allows isolation of the affected segment and permits subsequent targeted application of beneficial agents to the affected arterial segment.

The double balloons thus function to seal off or occlude a section of the vessel apart from performing a dilatation function to expand the opening of a plaque-ridden, stenotic area of the vessel. During this occlusion step, the surfaces of the balloons contact healthy vessel tissue. Pressurizing and inflating the balloons to contact healthy endothelial or endoluminal tissue can cause injury to such tissue. The first kind of injury arises from abrading and compressing the surface cells of the inner vessel wall, which may lead to denuding of the surface, when the occlusion balloons are inflated. Denuding of the vessel wall may initiate the restenosis process. Another kind of injury, disruption of the internal elastic lamina, may be sustained because of the pressures that may be needed to provide a seal between the occlusion balloons and the vessel surfaces; this injury may result in distension of the vessel wall. Thus, certain balloon pressures may also cause injury to healthy vessel wall.

Hence, a comparative disadvantage of using a double-balloon catheter for delivery of biologically active agents is that the balloons must contact healthy portions of the inner wall of the vessel being treated, unlike a catheter with only a single dilatation balloon which generally only touches the plaque-covered vessel wall in their dilatation function of opening the stenotic segment. A double-balloon catheter, however, contacts not only the plaque-ridden part of the vessel during the dilatation step, but also touches at least two healthy, unaffected areas of the vessel during the occlusion step when both balloons are inflated. Accordingly, there exists a need for an improved double-balloon catheter that minimizes the denuding of healthy endothelial or endoluminal tissue due to abrasion and compression by the occlusion balloons when they are inflated.

The present invention applies to a catheter having two or more occlusion balloons wherein the balloons are spaced apart, and the balloons are simultaneously inflated to form a sealed space in a portion of a body lumen or an occluded portion in the body lumen. An object of the present invention is to provide a balloon catheter that reduces abrasion-type damage to healthy endothelial or endoluminal tissue.

Yet another object of the invention is to provide a double-balloon catheter having at least two balloons dispensing biologically active agents in the targeted area of the occluded portion of the body lumen situated between the occlusion balloons. Such balloons may provide superior sealing, can concurrently permit the use of comparatively lower balloon inflation pressures. The advantage of using lower pressures to achieve sufficient sealing is that the distension of the lumen wall may be reduced when the occlusion balloons are inflated.

Another object of the present invention is to provide a method to seal a targeted space within the body lumen which is to be treated with a biologically active agent, while facilitating more effective sealing and less injury to the endothelial or endoluminal wall. Moreover, by dispensing the biologically active agent in a targeted area that is effectively sealed, the present invention provides a more efficient and economical method of dispensing the biologically active agents and treating a body lumen.

SUMMARY OF THE INVENTION

The present invention provides in one aspect, a balloon catheter for occluding two ends of a portion of a body lumen and treating the occluded portion. The catheter comprises at least two balloons each having an exterior surface and a catheter segment connectively placed between the balloons. A coating comprising a hydrogel polymer is applied to the exterior surface of each of the occlusion balloons. The presence of such hydrogel on the occlusion balloons reduces the damage to the endothelial tissue of the body lumen that contacts the balloon upon expansion. The balloons are capable of being inflated and deflated within the body lumen, and when both balloons are inflated, form a substantially closed space within the occluded portion of the body lumen by forming a seal between the balloon surface and inner wall surface of the body lumen. The catheter segment is capable of delivering a biologically active agent to the occluded portion of the body lumen.

Embodiments of the balloon catheter may incorporate one or more of the following features. The delivery of the biologically active agent may be conducted using a plurality of holes or ports extending through the catheter wall of the catheter segment connecting the balloons. The holes or ports fluidly connect an inner lumen of the catheter segment and its exterior. The holes or ports are located between the balloons, and permit the biologically active agent to pass through from the inner catheter lumen to the exterior of the catheter segment. Other methods of delivering biologically active agents may also be employed with this multi-balloon catheter so long as the material is delivered between the balloons. The balloons can be made of an expandable material or a material that is substantially non-expandable, although the balloons are inflatable in either case.

The biologically active agents that can be used may have various effects. For example, it may be an anti-inflammatory drug which reduces body reaction to tissue injury, or it may be an anti-proliferative agent which is capable of blocking smooth muscle cell proliferation, in particular, as a reaction to tissue injury or irritation. The biologically active agents used may be dispensed through holes or ports in the catheter wall.

The exterior of both balloons are coated with a coating comprising a hydrogel polymer, which is preferably tenaciously adhering on the balloon surface. This coating can be variously manufactured to have different thicknesses in its dry and hydrated states. The hydrogel polymer may be selected from poly-carboxylic acids, celluosic polymers, gelatin polyvinyl-pyrrolidone, maleic anhydride polymers, polyamides, polyvinyl alcohols, and polyethylene oxides. The hydrogel coating may be substantially free of a biologically active agent.

In another aspect of the invention, the coating comprising a hydrogel polymer over the exterior of the balloons may be loaded with a biologically active agent within the hydrogel matrix. The coating over the balloons may be used to deliver biologically active agents to proactively treat the healthy, inner lining of the body lumen that contacts the coating. Suitable biologically active agents should be capable of being incorporated into a hydrogel matrix which can leach or elute out on when pressure is applied to the hydrogel coating the balloon surfaces. It will be appreciated that the hydrogel coating of a multi-balloon catheter may optionally contain a biologically active agent to treat the contact area of healthy endothelial lumen tissue. This is a separate treatment modality, distinct from the treatment modality wherein the biologically active agent is delivered from within the catheter to treat the plaque-affected segment of the lumen that is contained in the space formed by inflation of the balloons or occluded portion of the body lumen.

In yet another aspect, a three-balloon catheter is provided, where the two outer balloons can be occlusion balloons and the middle balloon can be a dilatation or occlusion balloon. The two outer occlusion balloons can have a coating of hydrogel which is generally free of any therapeutic, biologically active agents since they contact only healthy vessel tissue. The middle, dilatation or occlusion balloon can be coated with a hydrogel which may be loaded with a biologically active agent to treat the target site of the vessel.

In a further aspect of the invention, the entire exterior surface of the catheter as well as the balloons may be coated with a hydrogel for ease of manufacture.

In yet another aspect of the invention, a method is provided for treating a body lumen using a multi-balloon catheter that maintains the integrity of the endothelial cells of the body lumen, the method comprising: inserting a catheter having at least two spaced-apart balloons into the body lumen, wherein the balloons are coated with a coating comprising a hydrogel polymer; inflating both balloons to contact the endothelial or cells of the inner wall of the body lumen; forming a substantially closed space between the balloons within the body lumen; and providing a biologically active agent into the closed space to treat a portion of the body lumen.

BRIEF DESCRIPTION OF THE DRAWINGS

The present invention will be explained with reference to the following drawings.

FIG. 1 is a perspective view of an embodiment of a double-balloon catheter with both balloons inflated;

FIG. 2 is a cross-sectional view of the catheter of FIG. 1 showing the inner channels at section A—A of FIG. 1;

DETAILED DESCRIPTION OF THE PREFERRED EMBODIMENTS

Figure 3:
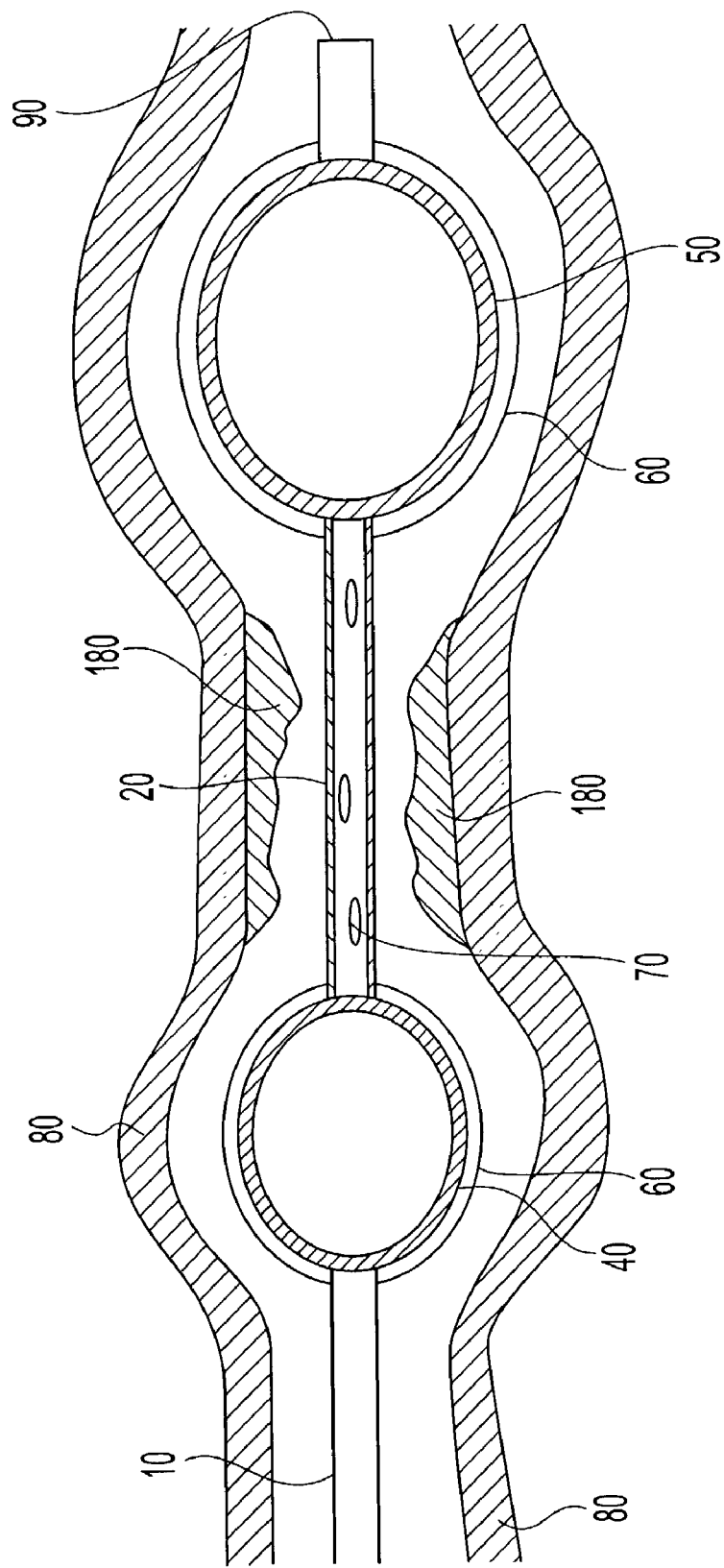
FIG. 3 is longitudinal cross-sectional view of a catheter of the present invention inserted within a stenotic blood vessel with both balloons inflated, this embodiment shows the hydrogel coating on the occlusion and dilatation balloons and also the plaque on the vessel inner wall.

FIG. 1 shows an exemplary embodiment of the catheter assembly having two spaced-apart balloons, the occlusion balloon 40 and dilatation/occlusion balloon 50. The outer catheter 10 is configured with two lumina (not shown). The two balloons may be made of an expandable material or a substantially non-expandable material such as polyurethanes. In either case, the balloons are inflatable and thus capable of pushing against the inner wall of the body vessel once they are inserted. The catheter has a distal orifice 90, a metal marker 120 to enable x-ray identification of the location of the dilatation/occlusion balloon, and a catheter segment 20 that connects the two balloons. Extending through the orifice 90, a guidewire 34 has a stop plug 170 which can be used to cap the orifice 90. A coating comprising a hydrogel polymer (not shown) is applied to the exterior surface of balloons 40 and 50. A plurality of ports or holes 70 extend through the wall of the catheter segment 20 which permits a biologically active agent to pass from an inner lumen in the catheter segment 20 to the exterior of the catheter segment 20 and thereby target treatment to the section of the body lumen between the two balloons or the occluded portion of the body lumen. Also shown in FIG. 1 are a number of Y connectors, 140 and 160 with side ports 130 and 150, respectively. Connections 100 and 110 are inputs connected to balloons 40 and 50, respectively, for supplying a pressurizing medium.

The catheter shown in FIG. 1 is only one example of a catheter suitable for the present invention. Other catheter designs can also be employed in this invention. The skilled artisan is aware of such additional suitable catheter designs.

FIG. 2 shows an exemplary embodiment of a cross-sectional view of the catheter of FIG. 1 at section A—A. The outer catheter is shown with two lumens 35 and 33. An inner catheter stem 31 is shown inserted into lumen 33 and this stem 31 has two lumens 30 and 32. This view shows that four different lumens can be used to provide independent pressure control to occlusion balloon 40 and dilatation/occlusion balloon 50, to deliver a biologically active agent through the holes 70, and to receive the guidewire 34. The outer catheter 10 is configured with two lumina. The lumen 35 serves to supply the pressurizing medium to the occlusion balloon 40 while the lumen 33 permits a biologically active agent to be delivered to a targeted vessel portion. The lumen 30 serves to supply the pressurizing medium to dilatation/occlusion balloon 50 while lumen 32 can be used to receive guidewire 34. It should be noted that this is only one of many embodiments that can be used to independently control the inflation and deflation of the two balloons as well as to provide a separate fluid channel for the biologically active agents to travel and exit from the holes or plurality of holes 70. Generally, there should be at least three separate channels within the catheter to service the two balloons and to deliver the biologically active agents through the catheter holes 70.

FIG. 3 shows, in accordance with the present invention, a longitudinal cross-sectional view of a catheter of the present invention that has been inserted within a blood vessel 80 with both balloons 40 and 50 inflated. This embodiment shows the coating comprising a hydrogel polymer 60 over the exterior surface of the occlusion and dilatation/occlusion balloons and also the plaque 180 on the vessel inner wall. FIG. 3 shows the subsequent position of the two balloons following the step in which the plaque-lined vessel has been previously dilated by inflating the dilatation/occlusion balloon 50 at the site of the plaque 180. After the expansion of the plaque site, the catheter is moved to re-position the two balloons such that the target area of the vessel having the plaque 180 on the vessel wall 80 is between the occlusion balloon 40 and dilatation/occlusion balloon 50.

In operation, the double-balloon catheter described in FIGS. 1–3 is advanced into a body lumen such as an arterial vessel until the dilatation/occlusion balloon 50 is precisely located at the stenotic site, while the location of the balloon 50 is monitored by x-ray with the aid of a metal marker 120 attached to the inner stem 31 within the dilatation/occlusion 50 balloon. By supplying a pressurizing medium via the connection 110 the dilatation balloon 50 can be inflated, dilating the stenotic, plaque-coated site of the lumen. Once this dilatation action has been completed, the pressurizing medium is drained from the dilatation balloon 50 and the catheter is advanced into the body lumen beyond the plaque-coated site until the dilatation balloon 50 is downstream, while the occlusion balloon 40 remains located in a portion upstream of the treated segment of the body lumen. Then, a pressurizing medium is supplied to the two balloons via the connections 100 and 110 so that both balloons are inflated to isolate the plaque-coated segment of the body lumen and form an occluded portion of the body lumen. The balloons are internally pressurized to between about 1 to 10 atmospheres and preferably between about 1 to 6 atmospheres to provide a seal between the hydrogel coated surface of each balloon and the healthy, endothelial tissue of the body lumen wall. In this inflated state, the two balloons form a substantially fluid-tight, enclosed space which contains the segment of body lumen wall to be treated. A biologically active agent can be delivered into this occluded portion of the body lumen from the holes 70 while the balloons 40 and 50 remain inflated. The biologically active agent can be delivered via the connection 150 of the Y connector 160 into the occluded portion of the body lumen between the two balloons 40 and 50. After delivery of the biologically active agent for a period of seconds to 10 minutes, the excess fluid can be drawn out from the occluded portion of the body lumen through the ports 70 and into the inner stem 20 of the inner catheter and via the guidewire lumen 32. It is also possible to deliver the biologically active agent via the guidewire lumen 32 of the inner catheter and to drain the biologically active agent via the lumen 33 in the outer catheter.

With this embodiment, throughout the duration of treatment, the guidewire 34 must be retracted in the guidewire lumen 32 sufficiently so that occlusion element 170 abuts the orifice 90 to cap it. Once the orifice is sealed, the guidewire lumen 32 can be employed as the lumen for supply and removal of the biologically active agent.

After the biologically active agent is allowed to react with the target plaque and endothelial tissue of the body lumen upon which the plaque is deposited, and after the excess biologically active agent has been drawn off from the occluded portion of the body lumen formed by the two inflated balloons, the pressurizing medium is drawn off from the two balloons to deflate them. With the treatment procedure thus completed, the catheter assembly is removed from the body lumen.

When plaque build-up is the cause of stenosis, the catheter having a balloon with a dual dilatation/occlusion function, as shown in FIG. 1, can be used. Many other treatments, however, do not require a balloon having a dilatation function. Instead, two occlusion balloons can be inflated to seal a vessel portion, wherein a biologically active agent may be delivered into this sealed portion. For example, preventing the recurrence of arterial thrombus in a vessel may be accomplished by isolating the affected portion of the vessel and delivering a biologically active agent, such as an anti-proliferative or anti-thrombogenic into the isolated portion. Because the balloons function only to occlude a vessel and touch healthy vessel wall which are especially susceptible to de-nuding, a catheter having two hydrogel-coated balloons which are generally free of any biologically active agents, in accordance with the present invention, can be used to substantially reduce the potential for vessel damage. Additionally, the balloons may be further optimized to reduce potential abrasion to the healthy tissue by being made more compliant than a typical dilatation balloon.

In accordance with the present invention, isolation of a vessel may be accomplished with another embodiment of the invention wherein a catheter has three balloons, each coated with hydrogel. A three balloon catheter can occlude two different sections of a target vessel simultaneously or at different times. Each balloon would be accessible through an independent catheter channel, and a separate channel or channels would be used to deliver the biological agent from the holes 70 in the catheter segments 20 between the balloons. A catheter having more than three balloons is also possible, restricted only by the complexity of needing additional channels within the catheter, and the physical limitations thereon.

Figure 4:
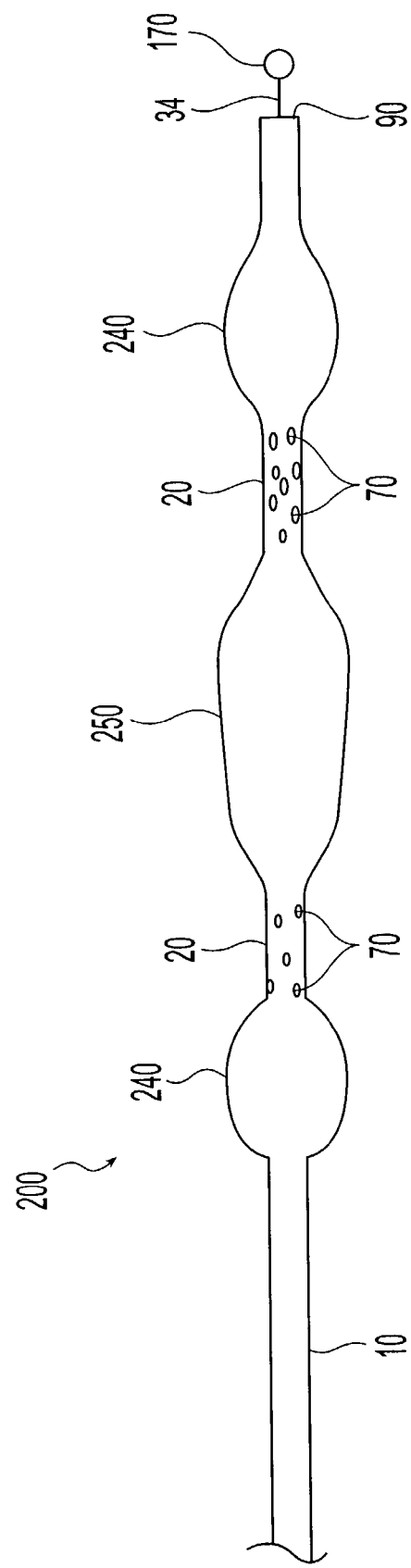
FIG. 4 shows an embodiment of a catheter having a plurality of balloons.

FIG. 4 shows one embodiment of a three-balloon catheter 200, wherein the middle balloon 250 may be used to dilate the stenotic (lesion) portion of the vessel and the outer balloons 240, which contact only healthy vessel tissue and thus coated with hydrogel, can serve as the occlusion balloons for isolating the treatment portion of the vessel. The expandability of the middle 250 and outer balloons 240 can be chosen to optimize their respective functions. Because balloon abrasion to a vessel lesion is less of a concern than abrasion to healthy tissue, the dilatation balloon may be designed to be less expandable than an occlusion balloon and employ higher pressures (up to 20 atms).

In operation the middle, dilatation balloon 250 may be inflated to dilate the stenotic area of the vessel. The middle, dilatation balloon 250 is deflated. Then the two, outer occlusion balloons 240 may be inflated to isolate the treatment portion of the vessel and a biologically active agent, e.g., cells or viral vectors may be delivered via the catheter into the enclosed space to treat the vessel wall.

In an alternative gene delivery embodiment, a three-balloon catheter 200 is used to apply the viral vector (or other agent) present in the coating on the middle balloon 250 (not necessarily a dilatation). When the middle balloon 250 is inflated, a therapeutic viral vector (or other agent) can be delivered via a diffusion process to the vessel wall. The two outer balloons 240 are inflated during this gene transfer process in order to provide vessel isolation. Optionally, in another embodiment of the method, in accordance with the present invention, another separate, biologically active agent can be delivered via holes 70 in the catheter in addition to the gene transfer procedure.

In another embodiment of the catheter of the present invention, the two outer balloons may be placed around a dispatch catheter. The dispatch catheter has a coil frame which permits delivery of biologically active agents, while the two outer balloons provide isolation of the vessel portion being treated.

There are a number of preferred variations of the present invention of the balloon catheters with hydrogel coating as provided in FIGS. 1–4. The first variation has an apparatus for delivering a biologically active agent situated between two spaced-apart, hydrogel coated balloons, but, morever, provides an additional treatment functionality in that the hydrogel is a matrix containing a biologically active agent that is delivered to the vessel wall when pressure is applied to the hydrogel coating on the balloon. Another variation builds on the above first or second variation. In this embodiment, the hydrogel coats not only the balloons, but also coats the entire catheter. This latter embodiment may be advantageous because it may be easier and less costly to manufacture. The hydrogel coating disposed over the surface of the balloons and, optionally, over the remaining surface of the catheter may or may not contain eluting biologically active agents.

Thus, the present invention provides a method for treating a body lumen using a multi-balloon catheter that maintains the integrity of the endothelial cells of the inner wall of the body lumen. The method comprises: (a) inserting a catheter having at least two balloons into the body lumen, wherein the balloons are coated with a coating comprising a hydrogel polymer; (b) inflating both balloons to contact the endothelial cells of the inner wall of the body lumen; (c) forming a substantially closed space between the balloons within the body lumen; and (d) providing a biologically active agent into the closed space.

The last step may be accomplished in various ways. However, a preferred means is to deliver the biologically active agent through a channel or inner lumen in the catheter segment connecting the two balloons. The inner catheter lumen is fluidly connected to holes 70 or ports extending through the walls of the catheter segment 20 which is connectively between the two spaced-apart balloons. The holes 70 permit the biologically active agent to pass through or be ejected from an inner catheter lumen to the exterior of the catheter segment 20.

An important element of the method is the use of hydrogel coated balloons to contact healthy endothelial cells in the body lumen during the occlusion step. There are several advantages provided by using hydrogel coated balloons. The hydrogel, which may be described alternatively as a foam, provides a cushioning interface between the balloon and the healthy body lumen cell lining. The cushioning can reduce the abrasion of the cells and consequent de-nuding of the body lumen when the balloons are inflated. Additionally, the hydrogel may help to create an effective sealant between the balloon and the body lumen, which may enable a reduction in pressure needed to inflate the balloons. Less pressure may reduce distension of the body lumen and thereby potentially reduce damage and irritation to the contact areas of the body lumen. In sum, the injury to the body lumen at the contact areas can be reduced.

The presence of the coating comprising a hydrogel polymer over the surface of balloons is, thus, a key element to the multi-balloon catheter of the present invention. The hydrogel polymer may be a cross-linked polymer material formed from the combination of a colloid and water. Preferably, the hydrogel is tenaciously adhering to the balloon surface, so that the hydrogel does not separate when the balloon is inflated within a body lumen. Cross-linking can reduce solubility and produce a jelly-like polymer that is characterized by the ability to swell and absorb a substantial amount of the drug, usually in aqueous solution form. The hydrogel coating is preferably hydrophilic, water swellable, and lubricious (i.e., having low coefficient of friction). Preferred hydrogels are polyacrylic acid and polymers available as HYDROPLUS® (Boston Scientific Corporation). Some other examples of materials from which hydrogels may be manufactured include poly-carboxylic acids, cellulosic polymers, gelatin polyvinyl-pyrrolidone, maleic anhydride polymers, polyamides, polyvinyl alcohols, and polyethylene oxides. Additional details concerning materials for making hydrogels are provided in U.S. Pat. Nos. 5,304,121, and 5,954,706, both issued to Sahatjian, and U.S. Pat. Nos. 5,674,192, and 5,843,049 issued to Sahatjian et. al.

In particular U.S. Pat. No. 5,304,121, Example 1, provides one method of producing hydrogel coated balloon using a "dipping" process. The surface of the balloon (polyethlene) of an angiographic catheter is prepared by wiping down with clean cloth. The balloon has an O.D. (outer diameter) of about 3.5 mm (inflated). The balloon is coated with a solution of 4,4 diphenylmethane diisocyanate (MDI) in methylethylketone for 30 minutes. After drying in an air oven at 85° C. for 30 minutes, the balloon is dipped in a 1.7% solution of poly(acrylic acid) homopolymer having a molecular weight of about 3,000,000 in dimethylformamide (DMF) and tertiarybutyl alchohol. After drying at about 85° C. for 30 minutes, a smooth coating is obtained. The balloon is oven dried for 8 hours at 50° C. One function of the drying steps is to remove solvent from the coating. The surface of the balloon becomes instantly lubricious upon exposure to water. The polyisocynanate solution is at a concentration of about 0.5 to 10% by weight. The poly (carboxyl acid) to polyisocyanate molar ratio is generally about 1:1. The formation of the hydrogel is further described in U.S. Pat. No. 5,091,205.

In addition to the above "dipping" process, there are other methods for providing a hydrogel coating over a balloon including "spraying" the coating onto the balloon. While the "dipping" method is described above as an example, the present invention is not limited to the particular manufacturing method in which the hydrogel is applied to the balloon, and, indeed, is inclusive of all forms of making the hydrogel coated balloon.

In general, when dried, the hydrogel coating should be greater than about 0.5 microns in thickness and preferably in the range of about 1.0 to 10.0 micrometers in thickness. The hydrogel coating thickness can swell by about a factor of 6 to 10 or even more when the hydrogel is hydrated. More preferably, the thickness of the hydrated coating is about 10 to about 55 microns in the swelled, uncompressed state.

In one embodiment, the hydrogel can be loaded with a biologically active agent that is released when in contact with fluid or when inflation pressure is applied. This provides a way for further deactivating the body's inflammatory and cell proliferation responses caused by irritation when the balloon contacts the healthy cell lining in the body lumen. Here, the treatment is directed not to the body lumen that is plaque-affected, but to the healthy part of the body lumen that is especially susceptible to injury when a foreign object such as a catheter balloon abrades or compresses the body lumen cell lining or distends the body lumen. Also, the hydrogel composition and biologically active agent may be chosen for the purpose of a particular rate-of-release response characteristic, this being dependent on the hydrogel's degree of cross-linking, charge, structure, thickness, or sensitivity to compression, and the agent's solubility, particle size and charge. For example, the response characteristic of the hydrogel coating may be designed such that an application of compressive pressure urges delivery of the biologically active agent in about 10 minutes or less, with 10 minutes representing the outward duration a balloon catheter should be inside an arterial vessel.

One example of an embodiment in which the hydrogel includes a biologically active agent is the use of heparin with the hydrogel. Heparin is absorbed into the coating without complexing and is freely released therefrom. Such hydrogel-drug combination can deliver about half of the drug solution in response to pressures used for balloon angioplasty. In other particular embodiments, the hydrogel polymer includes acid groups and incorporates the biologically active agent which is anionic in nature and is bound by electrostatic attraction to cations in the coating, such as an ammonium cation.

With respect to suitable biologically active agents that are intended to be delivered through a catheter channel, the agent should be easily dispensed through small holes or ports in the catheter segment joining the balloons. These biologically active agents are, in general, placed into an aqueous solution. Various biologically active agents may be delivered including, anti-inflammatory drugs, such as heparin or heparin derivatives, Ppack (dextro-phenylalanine proline argine chloromethylketone), enoxaprin, hirudin, or aspirin (acetylsalicylic acid) or an anti-proliferative agent, such as heparin (which has antiproliferative properties), enoxaprin, angiopeptin, or monoclonal antibodies capable of blocking smooth muscle cell proliferation. Dosages applied to the body lumen tissue, for example, of heparin are in the range of 10–30 mg of heparin solution containing 200–1000 units of sodium heparin.

Other examples of biologically active agents include thrombolytic agents, such as the enzyme, urokinase, which can be used to remove existing arterial thrombus. The term "biologically active material" encompasses therapeutic agents, such as drugs, and also genetic materials and biological materials. The genetic materials mean DNA or RNA, including, without limitation, of DNA/RNA encoding a useful protein stated below, anti-sense DNA/RNA, intended to be inserted into a human body including viral vectors and non-viral vectors. Examples of DNA suitable for the present invention include DNA encoding anti-sense RNA tRNA or rRNA to replace defective or deficient endogenous molecules angiogenic factors including growth factors, such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor cell ccle inhibitors including CD inhibitors thymidine kinase ("TK") and other agents useful for interfering with cell proliferation, and the family of bone morphogenic proteins ("BMP's") as explained below. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, skeletal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7(OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. Alternatively or in addition, molecules capable of inducing an upstream or downstream effect of a BMP can be provided. Such molecules include any of the "hedgehog" proteins, or the DNA's encoding them. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

immunosuppressants such as sirolimus (RAPAMYCIN), tacrolimus, everolimus and dexamethasone, antineoplastic/antiproliferative/anti-miotic agents such as paclitaxel, 5-fluorouracil, cisplatin, vinblastine, vincristine, epothilones, methotrexate, azathioprine, halofuginone, adriamycin, actinomycin and mutamycin; endostatin, angiostatin and thymidine kinase inhibitors, and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Also, the biologically active materials of the present invention include nitric oxide adducts, which prevent and/or treat adverse effects associated with use of a medical device in a patient, such as restenosis and damaged blood vessel surface. Typical nitric oxide adducts include nitroglycerin, sodium nitroprusside, S-nitroso-proteins, S-nitroso-thiols, long carbon-chain lipophilic S-nitrosothiols, S-nitrosodithiols, iron-nitrosyl compounds, thionitrates, thionitrites, sydnonimines, furoxans, organic nitrates, and nitrosated amino acids, preferably mono-or poly-nitrosylated proteins, particularly polynitrosated albumin or polymers or aggregates thereof. The albumin is preferably human or bovine, including humanized bovine serum albumin. Such nitric oxide adducts are disclosed in U.S. Pat. No. 6,087,479 to Stamler et al. which is incorporated herein by reference.

A biologically active material may be encapsulated in micro-capsules by the known methods. Still other biologically active agents can be therapeutic genes which may be carried in viral vectors such as recombinant, nuclear-specific adenoviral β-galactosidase. The delivered genes may be used to treat vascular proliferative disease by increasing gene expression in vascular tissue.

Delivery of genes to a treatment site can be accomplished in several ways. The genes may be delivered as a viral solution through holes or ports in a double-balloon catheter wall after isolation of the vessel. Another method of delivering the gene to the site is by applying a gene vector to a balloon's hydrogel surface and then transferring the genes to vessel wall tissue by inflating the balloon. This balloon can be prepared, for example, with a viral solution of 25μl of a $1.7 \times 10^{11}$ PFU/ml adenoviral β-galactosidase stock solution which can be applied over the surface of a hydrogel-coated, catheter balloon. This particular method of gene transfer is described in "Analysis of Adenoviral Transport Mechanisms in the Vessel Wall and Optimization of Gene Transfer Using Local Delivery Genes" by Palasis et al., Human Gene Therapy, 11:237–246, Jan. 20, 2000.

The following experimental studies have been performed and illustrate the advantages of using a hydrogel coated balloon to contact healthy endothelium as compared to a non-coated balloon. The experimental protocol was in compliance with the Guide for Care and Use of Laboratory Animals (NIH publication no. 86-23, 1985). New Zealand White Rabbits were anesthetized with ketamine (10 mg/kg) and acepromazine (0.2 mg/kg) after premedication with xylazine (2 mg/kg). The bilateral external iliac arteries were used for all experiments. A balloon of a catheter having no hydrogel coating was inflated to about 6 atm, resulting in a balloon diameter of about 3 mm inside one iliac and then deflated after 2 or 30 minutes elapsed. A balloon of a catheter coated with three layers of a high molecular weight polyacrylic acid polymer, i.e., hydrogel, was inserted into the contralateral iliac and then inflated to about 6 atm then deflated after 2 or 30 minutes. Three days after this transduction, the animals were anesthetized and the iliac arteries were harvested. The harvested vessels were fixed in paraformaldehyde for 10 minutes and washed in phosphate buffered solution post-fixation. The vessels were later cut open longitudinally. Cross-sectional specimens were embedded in paraffin, sectioned into 5 micrometer sections, and counterstained with hematoxylin and eosin. Slides were observed using light microscopy. An examination of the vessel specimens treated with the hydrogel coated balloon showed very little or no visible damage to the endothelium whereas, the vessel specimen treated with the uncoated balloon evidenced noticeable damage to the endothelial wall. Thus, the hydrogel coating over the balloon clearly prevented subsequent damage to healthy vessel endothelium when a balloon was dilated against the endothelium.

It is to be understood that, while various embodiments of the invention have been described, the foregoing are intended only as exemplary embodiments and that other embodiments may be within the spirit and scope of the present invention. It is further understood that other advantages, modifications and embodiments may be within the scope of the present invention as defined by the appended claims. Furthermore, the references mentioned herein are incorporated herein by reference.

What is claimed is:

1. A balloon catheter for occluding two ends of a portion of a blood vessel and treating the occluded portion of the blood vessel comprising:

a first balloon and a second balloon, each having an exterior surface and a catheter segment connectively placed therebetween; and a coating comprising a hydrogel polymer applied to the exterior surfaces of each of the balloons, wherein said catheter segment is capable of delivering a biologically active agent to the occluded portion of the blood vessel and wherein said balloons are capable of being inflated and deflated within the blood vessel, and when the balloons are inflated, form a substantially fluid-tight, closed space between the first and second balloons.

2. The balloon catheter of claim 1, wherein said coating is between about 1.0 and about 10.0 micrometers in thickness.

3. The balloon catheter of claim 1, wherein said catheter segment comprises an inner lumen, and a catheter wall and wherein at least one port extends through the wall to the exterior of the catheter segment, said port permitting the biologically active agent to pass through from the inner lumen to the exterior of the catheter segment.

4. The balloon catheter of claim 1, wherein said biologically active agent is an anti-inflammatory drug comprising heparin, PpacK (dextro-phenylalanine proline argine chloromethylketone), enoxaprin, hirudin or aspirin.

5. The balloon catheter of claim 1, wherein said biologically active agent is an anti-proliferative agent comprising monoclonal antibodies capable of blocking smooth muscle cell proliferation, heparin or enoxaprin.

6. The balloon catheter of claim 1, wherein said hydrogel polymer comprises poly-carboxylic acids, celluosic polymers, gelatin polyvinyl-pyrrolidone, maleic anhydride polymers, polyamides, polyvinyl alcohols, or polyethylene oxides.

7. The balloon catheter of claim 6, wherein said polycarboxylic acid is a polyacrylic acid.

8. The balloon catheter of claim 1, wherein the thickness of the coating in a swelled, uncompressed state is between about 10 to about 50 microns.

9. The balloon catheter of claim 1 which comprises a third-balloon disposed between the first and second balloons and a catheter segment connectively placed between the first and third balloons and a catheter segment connectively placed between the second and third balloons.

10. A balloon catheter for occluding two ends of a portion of a blood vessel and treating the occluded portion of the blood vessel comprising:
a first balloon and a second balloon, each having an exterior surface and a catheter segment connectively placed therebetween; and
a coating comprising a hydrogel polymer applied to the exterior surfaces of each of the balloons,
wherein said catheter segment is capable of delivering a biologically active agent to the occluded portion of the blood vessel and wherein said balloons are capable of being inflated and deflated within the blood vessel, and when both balloons are inflated, form a substantially fluid-tight, closed space between the first and second balloon, and wherein said coating is substantially free of any biologically active agent.

11. The balloon catheter of claim 10, wherein said coating is between about 1.0 and about 10.0 micrometers in thickness.

12. The balloon catheter of claim 10, wherein said catheter segment comprises an inner lumen, and a catheter wall and wherein at least one port extends through the wall to the exterior of the catheter segment, said port permitting the biologically active agent to pass through from the inner lumen to the exterior of the catheter segment.

13. The balloon catheter of claim 10, wherein said biologically active agent is an anti-inflammatory drug comprising heparin, PpacK (dextro-phenylalanine proline argine chloromethylketone), enoxapirin, hirudin or aspirin.

14. The balloon catheter of claim 10, wherein said biologically active agent is an anti-proliferative agent comprising monoclonal antibodies capable of blocking smooth muscle cell proliferation, heparin or enoxaprin.

15. The balloon catheter of claim 10, wherein said hydrogel polymer comprises poly-carboxylic acids, celluosic polymers, gelatin polyvinyl-pyrrolidone, maleic anhydride polymers, polyamides, polyvinyl alcohols, or polyethylene oxides.

16. The balloon catheter of claim 15, wherein said polycarboxylic acid is a polyacrylic acid.

17. The balloon catheter of claim 10, wherein the thickness of the coating in a swelled, uncompressed state is between about 10 to about 50 microns.

18. The balloon catheter of claim 10 which comprises a third-balloon disposed between the first and second balloons and a catheter segment connectively placed between the first and third balloons and a catheter segment connectively placed between the second and third balloons.

19. A method for treating a body lumen using a double-balloon catheter that maintains the integrity of the endothelial cells of the inner wall of the body lumen, the method comprising:
(a) inserting a catheter having at least two balloons into the body lumen, wherein the balloons are coated with a coating comprising a hydrogel polymer;
(b) inflating both balloons to contact the endothelial cells of the inner wall of the body lumen;
(c) forming a substantially closed space between the balloons within the body lumen; and
(d) providing a biologically active agent into the closed space.

20. The method of claim 19, wherein the coating is between about 1.0 and about 10.0 micrometers in thickness.

21. The method of claim 19, wherein the step of providing a biologically active agent is accomplished by providing a catheter segment between the two balloons, wherein the catheter segment has an inner lumen and a catheter wall, and at least one port extending through the wall, said port permitting the biologically active agent to pass through from the inner catheter lumen to the exterior of the catheter segment.

22. The method of claim 19, wherein the biologically active agent is an anti-inflammatory drug selected from the group consisting of heparin, PpacK (dextro-phenylalanine proline argine chloromethylketone), enoxaprin, hirudin and aspirin.

23. The method of claim 19, wherein the biologically active agent is an anti-proliferative agent selected from the group consisting of monoclonal antibodies capable of blocking smooth muscle cell proliferation, heparin and enoxaprin.

24. The method of claim 19, wherein said hydrogel polymer is selected from the group consisting of poly-carboxylic acids, celluosic polymers, gelatin polyvinyl-pyrrolidone, maleic anhydride polymers, polyamides, polyvinyl alcohols, and polyethylene oxides.

25. The method of claim 24, wherein said poly-carboxylic acid is a polyacrylic acid.

26. The method of claim 19, wherein the thickness of the coating in a swelled, uncompressed state is between about 10 to about 50 microns.

27. A method for treating a body lumen using a double-balloon catheter that maintains the integrity of the endothelial cells of the inner wall of the body lumen, the method comprising:
(a) inserting a catheter having at least two balloons into the body lumen, wherein the balloons are coated with a coating comprising a hydrogel polymer, and wherein said coating is substantially free of any biologically active agent;
(b) inflating both balloons to contact the endothelial cells of the inner wall of the body lumen;
(c) forming a substantially closed space between the balloons within the body lumen; and
(d) providing a biologically active agent into the closed space.

28. The method of claim 27, wherein the coating is between about 1.0 and about 10.0 micrometers in thickness.

29. The method of claim 27, wherein the step of providing a biologically active agent is accomplished by providing a catheter segment between the two balloons, wherein the catheter segment has an inner lumen and a catheter wall, and at least one port extending through the wall, said port permitting the biologically active agent to pass through from the inner catheter lumen to the exterior of the catheter segment.

30. The method of claim 27, wherein the biologically active agent is an anti-inflammatory drug selected from the group consisting of heparin, PpacK (dextro-phenylalanine proline argine chloromethylketone), enoxaprin, hirudin and aspirin.

31. The method of claim 27, wherein the biologically active agent is an anti-proliferative agent selected from the group consisting of monoclonal antibodies capable of blocking smooth muscle cell proliferation, heparin and enoxaprin.

32. The method of claim 27, wherein said hydrogel polymer is selected from the group consisting of poly-carboxylic acids, celluosic polymers, gelatin polyvinyl-pyrrolidone, maleic anhydride polymers, polyamides, polyvinyl alcohols, and polyethylene oxides.

33. The method of claim 32, wherein said poly-carboxylic acid is a polyacrylic acid.

34. The method of claim 27, wherein the thickness of the coating in a swelled, uncompressed state is between about 10 to about 50 microns.

* * * * *